United States Patent
Jaramillo Botero et al.

(10) Patent No.: US 11,977,049 B2
(45) Date of Patent: May 7, 2024

(54) FIELD-EFFECT NANOSENSOR FOR DETECTING SIMPLE METABOLITES IN LIVING ORGANISMS

(71) Applicant: PONTIFICIA UNIVERSIDAD JAVERIANA, Bogota (CO)

(72) Inventors: Andres Jaramillo Botero, Bogota (CO); Juan Manuel Marmolejo Tejada, Bogota (CO)

(73) Assignee: PONTIFICIA UNIVERSIDAD JAVERIANA, Bogota (CO)

( * ) Notice: Subject to any disclaimer, the term of this patent is extended or adjusted under 35 U.S.C. 154(b) by 572 days.

(21) Appl. No.: 17/270,169

(22) PCT Filed: Aug. 21, 2019

(86) PCT No.: PCT/IB2019/057061
§ 371 (c)(1),
(2) Date: Feb. 22, 2021

(87) PCT Pub. No.: WO2020/039377
PCT Pub. Date: Feb. 27, 2020

(65) Prior Publication Data
US 2021/0239645 A1    Aug. 5, 2021

(30) Foreign Application Priority Data
Aug. 21, 2018 (CO) .................... NC2018/0008743

(51) Int. Cl.
*G01N 27/414* (2006.01)
*G01N 27/30* (2006.01)
(Continued)

(52) U.S. Cl.
CPC ......... *G01N 27/414* (2013.01); *G01N 27/308* (2013.01); *G01N 33/483* (2013.01);
(Continued)

(58) Field of Classification Search
CPC .............. G01N 27/414; G01N 27/308; G01N 27/4145; G01N 27/4146; G01N 33/483;
(Continued)

(56) References Cited

U.S. PATENT DOCUMENTS 7,964,347 B2 *   6/2011   Dimitrov ......... G01N 33/54326
                                                 536/24.31
2012/0145549 A1   6/2012   Cho et al.
(Continued)

FOREIGN PATENT DOCUMENTS

WO   2006083269 A2   8/2006
WO   2016112079 A1   7/2016

OTHER PUBLICATIONS

Avouris et al., "Carbon-based electronics", Nature Nanotechnology, vol. 2, pp. 605-625, Oct. 2002.*
(Continued)

*Primary Examiner* — Nikolay K Yushin
(74) *Attorney, Agent, or Firm* — Hoglund & Pamias, PSC; Roberto J Rios

(57) ABSTRACT

The present invention discloses a sensor based on a field effect transistor (FET) with nano-tapes of a carbon-based material, especially graphene (GNR), a semiconductor joint, electrodes and a base gate composed of a carbon-based metallic material for the detection and measurement of low concentrations (nM-pM) of metabolites (biomarkers) in living organisms. The device features a unique nano-tape configuration of a carbon-based material, especially armchair-type graphene (GNR) (Armchair) in the semiconductor gasket and electrodes, which favors the manufacture of high-density nanosensor arrangements. The device features bifunctional ligaments based on pyrene compounds bound (Continued)

to the semiconductor joint and covalently the target analyte, generating the mechanical, chemical and electronic stability of the detected signal.

10 Claims, 4 Drawing Sheets

(51) Int. Cl.
| | |
|---|---|
| G01N 33/483 | (2006.01) |
| H01L 29/00 | (2006.01) |
| H01L 29/49 | (2006.01) |
| B82Y 30/00 | (2011.01) |
| B82Y 40/00 | (2011.01) |

(52) U.S. Cl.
CPC .............. H01L 29/49 (2013.01); B82Y 30/00 (2013.01); B82Y 40/00 (2013.01)

(58) Field of Classification Search
CPC ...... G01N 33/487; G01N 33/00; G01N 27/30; B82Y 30/00; B82Y 40/00; B82Y 10/00; H10K 99/00; H01L 29/49; H01L 29/0665; H01L 29/66795; H01L 29/1602
See application file for complete search history.

(56) References Cited

U.S. PATENT DOCUMENTS

| | | | | |
|---|---|---|---|---|
| 2015/0158850 | A1* | 6/2015 | Fasel | C07D 239/72 544/245 |
| 2016/0017416 | A1* | 1/2016 | Boyanov | C12Q 1/6825 506/4 |
| 2019/0376925 | A1* | 12/2019 | Choi | G01N 33/48721 |

OTHER PUBLICATIONS

T. Gan and S. Hu, "Electrochemical sensors based on graphene materials," Microchimica Acta, vol. 175, No. 1, p. 1, Jul. 2011. [Online]. Available: https://doi.org/10.1007/s00604- 011- 0639- 7.
J.S. Y. Chia, M. T. Tan, P. S. Khiew, J. K. Chin, and C. W. Siong, "A bio-electro senschemicaling platform for glucose based on irreversible, non-covalent pi-pi functionalization of graphene produced via a novel, green synthesis method," Sensors and Actuators B: Chemical, vol. 210, pp. 558-565,2015. [Online]. Available: http://www.sciencedirect.com/science/article/pii/ S0925400515000398.
C.-Y. Chan, J. Guo, C. Sun, M.-K. Tsang, F. Tian, J. Hao, S. Chen, and M. Yang, "A reduced graphene oxide-au based electrochemical biosensor for ultrasensitive detection of enzymatic activity of botulinum neurotoxin a," Sensors and Actuators B: Chemical, vol. 220, pp. 131-137, 2015. [Online]. Available: http://www. sciencedirect. com/science/article/pii/S0925400515006711.
X. Zhang, F. Gao, X. Cai, M. Zheng, F. Gao, S. Jiang, and Q. Wang, "Application of graphene-pyrenebutyric acid nanocomposite as probe oligonu-cleotide immobilization platform in a dna biosensor," Materials Science and Engineering: C, vol. 33, No. 7, pp. 3851-3857, 2013. [Online]. Available: http://www.sciencedirect.com/science/article/pii/S092849311300310X.
J. Tian, P.-X. Yuan, D. Shan, S.-N. Ding, G.-Y. Zhang, and X.-J. Zhang, "Biosensing platform based on graphene oxide via self-assembly induced by synergic interactions," Analytical Biochemistry, vol. 460, pp. 16-21, 2014. [Online]. Available: http://www.sciencedirect.com/science/article/pii/S0003269714002280.
Wenlong Yang, Andrea Lucotti, Matteo Tommasini, and Wesley A. Chalifoux "Bottom-Up Synthesis of Soluble and Narrow Graphene Nanoribbons Using Alkyne Benzannulations" J. Am. Chem. Soc. 138, 29, 9137-9144.
P.Hu, J.Zhang, L.Li, Z.Wang, W.O'Neill, andP. Estrela, "Carbon-nanostructure-based field-effect transistors for label-free chemical/ biological sensors," Sensors, vol. 10, No. 5, pp. 5133-5159, 2010.

[Online]. Available: http://www.mdpi.com/1424- 8220/10/5/5133.
T.T. Tranand, A. Mulchandani, "Carbon nanotubes and graphene nanofield-effect transistor-based biosensors," TrAC Trends in Analytical Chemistry, vol. 79, pp. 222-232, 2016, past, Present and Future challenges of Biosensors and Bioanalytical tools in Analytical Chemistry: a tribute to Prof Marco Mascini. [Online]. Available: http://www.sciencedirect.com/science/article/pii/ S0165993615301643.
Lulu Ren, Tianxi Liu, Juan Guo, Shuzhong Guo, Xiaoyan Wang and Weizhi Wang, "A smart pH responsive graphene/polyacrylamide complex via noncovalent interaction", Nanotechnology 21 (2010) 335701 (7pp).
Ying Wang, et al., "Bioinspired prospects of graphene: from biosensing to energy", J. Mater. Chem. B, 2013,1, 3521-3534.
Wang et al., "Electrostatic Assembly of Peptide Nanofiber-Biomimetic Silver Nanowires onto Graphene for Electrochemical Sensors", ACS Macro Lett. 2014, 3, 6, 529-533.
Sung Ho Song, et al., "Enhanced Thermal Conductivity of Epoxy-Graphene Composites by Using Non-Oxidized Graphene Flakes with Non-Covalent Functionalization", Advanced Materials, vol. 25, Issue 5, Feb. 6, 2013, pp. 732-737.
Y. H. Kwak, D. S. Choi, Y. N. Kim, H. Kim, D. H. Yoon, S.-S. Ahn, J.-W. Yang, W.S. Yang, and S. Seo, "Flexible glucose sensor using cvd-grown graphene-based field effect transistor," Biosensors and Bioelectronics, vol. 37, No. 1, pp. 82-87, 2012. [Online]. Available: http://www.sciencedirect.com/science/article/pii/ S0956566312002710.
P. Labroo and Y. Cui, "Flexible graphene bio-nanosensor for lactate," Biosensors and Bioelectronics, vol. 41, pp. 852-856, 2013. [Online]. Available: http://www. sciencedirect.com/science/article/ pii/S0956566312005489.
F. Liu, K. S. Choi, T. J. Park, S. Y. Lee, and T. S. Seo, "Graphene-based electrochemi- cal biosensor for pathogenic virus detection," BioChip Journal, vol. 5, No. 2, pp. 123-128, Jun. 2011. [Online]. Available: https://doi.org/10.1007/s13206- 011- 5204- 2.
D. Du, S. Guo, L. Tang, Y. Ning, Q. Yao, and G.-J. Zhang, "Graphene-modified electrode for dna detection via pna-dna hybridization," Sensors and Actuators B: Chemical, vol. 186, pp. 563-570, 2013. [Online]. Available: http://www.sciencedirect.com/science/ article/pii/S0925400513007260.
Nathaniel S. Green, Michael L. Norton, "Interactions of DNA with graphene and sensing applications of graphene field-effect transistor devices: A review", Analytica Chimica Acta 853 (2015) 127-142.
S.-R. Guo, J. Lin, M. Penchev, E. Yengel, M. Ghazinejad, C. S. Ozkan, and M. Ozkan, "Label free dna detection using large area graphene based field effect transistor biosensors," Journal of Nanoscience and Nanotechnology, vol. 11, No. 6, pp. 5258-5263, 2011. [Online]. Available: http://www.ingentaconnect.com/content/ asp/ jnn/2011/00000011/00000006/art00082.
Y. Ohno, K. Maehashi, K. Inoue, and K. Matsumoto, "Label-free aptamer-based immunoglobulin sensors using graphene field-effect transistors," Japanese Journal of Applied Physics, vol. 50, No. 7R, p. 070120, 2011. [Online]. Available: http: stacks.iop.org/1347-4065/50/i-7R/a-070120.
Hong Ying Mao, et al., "Manipulating the electronic and chemical properties of graphene via molecular functionalization", Progress in Surface Science 88 (2013) 132-159.
F. Liu, Y. H. Kim, D. S. Cheon, and T. S. Seo, "Micropatterned reduced graphene oxide-based field-effect transistor for real-time virus detection," Sensors and Actuators B: Chemical, vol. 186, pp. 252-257, 2013. [Online]. Available: http://www.sciencedirect.com/ science/article/pii/S0925400513006801.
Xuqiang Ji, et al., "Non-covalent interactions for synthesis of new graphene based composites", Composites Science and Technology 106 (2015) 25-31.
V. K. Kodali, J. Scrimgeour, S. Kim, J. H. Hankinson, K.M. Carroll, W. A. de Heer, C. Berger, and J. E. Curtis, "Nonperturbative chemical modification of graphene for protein micropatterning," Langmuir, vol. 27, No. 3, pp. 863-865, 2011, pMID: 21182241. [Online]. Available: http://dx.doi.org/10.1021/la1033178.
M. Hinnemo, J. Zhao, P. Ahlberg, C. Hagglund, V. Djurberg, R. H. Scheicher, S.-L. Zhang, and Z.-B. Zhang, "On monolayer formation of pyrenebutyric acid on graphene," Langmuir, vol. 33, No. 15, pp.

(56) References Cited

OTHER PUBLICATIONS 3588-3593, 2017, pMID: 28350965. [Online]. Available: http://dx.doi.org/10.1021/acs.langmuir.6b04237.

Wenjing Hong, et al., "Preparation of Gold Nanoparticle/Graphene Composites with Controlled Weight Contents and Their Application in Biosensors", J. Phys. Chem. C 2010, 114, 1822-1826.

D.-J.Kim, I.Y. Sohn, J.-H. Jung, O.J. Yoon, N.-E. Lee, and J.-S.Park, "Reduced graphene oxide field-effect transistor for label-free femtomolar protein detection," Biosensors and Bioelectronics, vol. 41, pp. 621-626, 2013. [Online]. Available: http://www.sciencedirect.com/science/article/pii/S095656631200646X.

C. X. Guo, S.R. Ng, S. Y. Khoo, X. Zheng, P. Chen, and C.M. Li, "Rgd-peptide functionalized graphene biomimetic live-cell sensor for real-time detection of nitric oxide molecules," ACS Nano, vol. 6, No. 8, pp. 6944-6951, 2012, pMID: 22793649. [Online]. Available: http://dx.doi.org/10.1021/nn301974u.

Wenchao Gao, et al., "Signal amplification of streptavidin-horseradish peroxidase functionalized carbon nanotubes for amperometric detection of attomolar DNA", Chem. Commun., 2011, 47, 5220-5222.

C. N. R. Rao, et al., "Some Novel Attributes of Graphene", J. Phys. Chem. Lett. 2010, 1, 572-580.

Julia Wind, et al., "Sucrose: Metabolite and signaling molecule", Phytochemistry 71 (2010) 1610-1614.

Jingquan Liu, et al., "Thermosensitive Graphene Nanocomposites Formed Using Pyrene-Terminal Polymers Made by RAFT Polymerization", Journal of Polymer Science: Part A: Polymer Chemistry, vol. 48, 425-433 (2010).

Mitchell B. Lerner, et al., "Toward Quantifying the Electrostatic Transduction Mechanism in Carbon Nanotube Molecular Sensors", J. Am. Chem. Soc. 2012, 134, 14318-14321.

B. Cai, S. Wang, L. Huang, Y. Ning, Z. Zhang, and G.-J. Zhang, "Ultrasensitive label-free detection of pna-dna hybridization by reduced graphene oxide field-effect transistor biosensor," ACS Nano, vol. 8, No. 3, pp. 2632-2638, 2014, pMID: 24528470. [Online]. Available: http://dx.doi.org/10.1021/nn4063424.

\* cited by examiner

FIELD-EFFECT NANOSENSOR FOR DETECTING SIMPLE METABOLITES IN LIVING ORGANISMS

FIELD OF INVENTION

The present invention relates to the technical field of metabolomics, in particular the processes of measurement of metabolites. In particular, the present invention refers to a sensor from carbon-based nanostructured materials for the detection of simple metabolites in living organisms.

BACKGROUND OF INVENTION

In the field of processes for the detection of molecules, carbon-based nanostructured materials, such as graphene, are of high interest in due to: (1) their high surface area by volume, maximizing its sensitivity to environmental effects, (2) its ability to allow surface functionalization in selective analyte detection, (3) its high biocompatibility by being composed of carbon atoms, (4) its stability and oxidation resistance in aqueous environments and low voltage operation, and (5) the availability of standard manufacturing techniques for commercial-scale devices.

In addition, its electrical properties are highly susceptible to donor analytes and electron receptors, enabling differentiation of absorbed molecules on their surface, as well as offering high carrier mobility (electrons or eggs), high electronic conductivity, wide chemical and thermodynamic stability, and high mechanical flexibility.

An important aspect of developing selective and accurate graphene-based sensors is surface functionalization. This, since covalent or non-covalent surface functionalization can provide mechanical, chemical and electronic stability in signal detection.

Non-covalent graphene functionalization is typically obtained by chemical groups that interact through weak $\pi$-$\pi$, van der Waals or electrostatic forces; while covalent functionalization is mainly obtained by nucleophilic substitution, electrophilic addition, condensation and addition reactions between the functional groups of molecules and oxygenated groups of graphene oxide (GO) or reduced graphene oxide (rGO) surfaces, such as epoxides and hydroxils in their basal planes and carboxyls at the edges.

In addition, the non-covalent functionalization of its surface with aromatic molecules allows to avoid significant changes in the transport and switching properties of GNRs. These functional aromatic groups are used as mechanical binders of target molecules with high sensitivity and selectivity to graphene, by promoting fissorption and improving reaction with target molecules. For example, Chen and collaborators demonstrated the use of pyrenbutanoic acid to functionalize the outer walls of carbon nanotubes, as well as other authors have demonstrated or use on graphene surfaces.

Putzback and Ronkainen reported the use of pyrenobutaneic acidimidyl succin ester binders for immobilizing enzymes in graphene, Kwak and collaborators for graphene-based glucose sensors, and Labroo and collaborators for the detection of lactate at different concentrations with graphene-based sensors.

Also, the succinyl ester pyrenobutaneic acid has been used as a binder in rGO to detect DNA and specific proteins.

The N-hydroxysuccinimide pyrenbutyric acid ester in GO or clean graphene results in stable, reproducible and high-sensitivity sensors and selectivity to glucose and rotavirus.

For its part, rGO-based sensors with PyBA binders have been shown to immobilize peptides, as a way to detect the enzymatic activity of neurotoxins and the response of human cells to drug stimuli thanks to the increase of electrochemical currents in the electrodes of the device. Finally, PyBA molecules have been functionalized in graphene with gold electrodes to detect DNA efficiently using blue methylene indicators.

In the field of related patents in the state of the art close to the invention document WO2016112079 is observed, which discloses graphene nanosensors to monitor an objective analyte using anti-target analyte aptamers; they can include a single conductance sensor on a substrate platform, where the graphene sensor can be functionalized with aptamers to bind to the target analyte, or alternatively, a non-sensor can include functionalized micro-pearls with aptamers that can allow selective enrichment and isocratic elution of the target analyte, where the concentration of the enriched target analyte can be measured on a functional graphene surface.

Document US20120145549 A discloses a nanosensor that includes a substrate that includes a hole that extends through the substrate, a thin layer on the substrate and includes a nanopore that is connected to the hole, and a first layer of graphene and a second layer of graphene that are in the thin layer and separated from each other by centering the nanopore between them. Similarly, it exposes a nanosensor manufacturing method from the formation of a nanopore into a thin layer on a substrate, and the formation of a first layer of graphene and a second layer of graphene on the thin layer. The first layer of graphene and the second layer of graphene are separated from each other by centering the nanopore between them.

Document WO2006083269 reveals a quantum-point protein luminescent biosensor that can be custom designed for the specific detection of environmentally or medicinally important compounds. This biosensor uses a nano-sized biomolecule-inorganic or organic assembly that serves as scaffolding for a fluorescence proficiency test. Specific and sensitive detection of chemical poisons, contaminants and biotoxins can be performed by mediating the structures within the biomolecule-nanoparticle assembly, while maintaining the luminescent properties of the generalized probe.

In these conditions, the present invention solves the problem related to the platforms of detection and measurement of metabolites (biomarkers) by means of a sensor based on materials from carbon with controlled geometric conditions that allows intracellular censusing of UDP and, indirectly, sucrose.

BRIEF DESCRIPTION OF THE INVENTION

A first object, the present invention discloses a device based on a field effect transistor for the nanometric sensing of molecules from carbon-based materials.

In a preferred mode, the width of the electrodes and the central joint of the nanosensor is controlled to obtain quasi-metallic or semiconductor behavior, respectively, allowing the control of electronic currents by external field effect. The central joint of the device, between the electrodes, based on graphene nano-tapes (GNRs), or narrow strips of graphene, is functionalized with self-assembled pyrenobutyric acid (PyBA) molecules that by binding to UDP-glucose molecules modify the electronic transport properties of the device.

The objects described above, as well as any additional objects, will be exposed in greater detail and sufficiency

DETAILED DESCRIPTION OF THE INVENTION

Figure 1A:
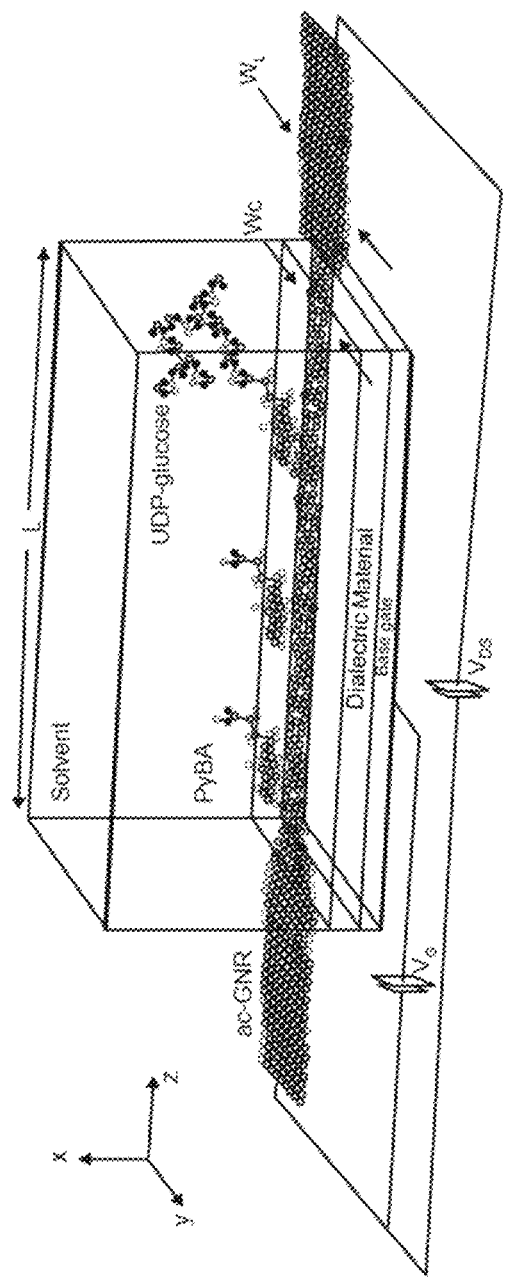
FIG. 1a. Isometric view of the graphene field effect sensor object of the invention with semiconductor channel in solvent, three molecules of pyrenobutyric acid and a udp glucose molecule covalently linked to one of these. (Pyrenobutyric acid is bound to graphene by non-covalent interactions). The figure shows a metal base gate that can be manufactured in graphene of any chirality and a separator dielectric material; in a preferred embodiment the dielectric material is boron nitride. The electrode on the left side slides the source gate and the right-side electrode to the drain gate.

The present invention arises in response to the need to incorporate platforms for the detection and measurement of primary metabolites, such as sucrose, starch, or intermediate by-products such as UDP-glucose, economically and with a high degree of precision, which allows to generate a significant improvement in disease monitoring and control mechanisms, as well as in the improvement of agricultural crops.

The description of the realization of the present invention is not intended to limit its scope, but to serve as a particular example of it. It is hoped that a person versed in the matter will understand that the equivalent embodiments do not depart from the spirit and scope of the present invention in its broadest form.

The present invention discloses a novel sensor based on a field effect transistor (FET) with nano-tapes of a carbon-based nanostructured material for indirect detection and measurement of simple metabolites.

In a preferred embodiment of the invention the chosen nanostructured material based on carbon is graphene, due, among other factors, to its large surface area by volume that maximizes the sensitivity of its physical properties to environmental effects, its easy functionalization of the surface to improve the selectivity of detection, its high degree of biocompatibility, its stability and resistance to oxidation in aqueous environments under low polarization operation.

The device also comprises a base composed of a carbon-based material or a metallic material. In a preferred embodiment of the invention the material of the base is graphene.

In a preferred embodiment of the invention, the sensor indirectly detects and performs the measurement of low concentrations (nM-pM) of sucrose by means of Uridine glucose diphosphate (UDP-glucose) from a molecule. This, since UDP-glucose is an intermediate reagent in the synthesis of sucrose inside the cytoplasm of a plant cell.

The sensor object of the present invention presents a unique configuration of GNRs.

Two-dimensional graphene is metallic by nature. However, graphene nano-tapes (GNRs) or narrow graphene strips, allow you to control electronic states, including the band structure of the material, depending on the structures of the edges (armchair or zigzag type).

In a preferred embodiment of the invention, the configuration of the GNRs is of Armchair type in the semiconductor channel and in the electrodes, which favors the manufacture of arrangements of high density nanosensors in circuits that allow conclusions on the collective state of biomarkers in an organism, which is useful in establishing and measuring complex variables from a logic of electronic devices commanded by the concentrations of biomarkers.

The GNR platform that incorporates the present invention is useful in the detection of different analytes, depending on the specific functional groups used in the specific embodiments of the central region of the sensor.

In the preferred embodiment of the invention, the transistor device (semiconductor joint and electrodes) is completely based on graphene nano-tapes with "armchair" edge (armchair), allowing the design of compact devices, which in turn allow circuits of high density and complexity.

In another embodiment of the invention, the electrodes are nano-tapes of graphene, zigzag type, or metallic material.

The nanoscale biomarker measurement device, made entirely of carbon, minimizes toxicity to living organisms, reduces harmful impacts on the environment, and allows the measurement of analytes at minimum concentrations, among other benefits.

The graphene semiconductor gasket also allows easy functionalization with different binding molecules, which enables selective detection of different analytes and a significant improvement in the relationship between electronic measurement signal and thermal noise on the nanoscale.

The use of graphene with "armchair" edge for source and drainage electrodes, and regardless of edge for the gate electrode (Brandimarte and collaborators demonstrated the use of graphene gates in field effect transistors), allows an efficient and compact design, with minimal surface footprint.

The present invention employs a wide variety of bifunctional ligands based on pyrene, which allows selective detection of a wide number of different biomarkers. This effect is generated by the functionalization of the surface of the central GNR by the pyrene end by non-covalent forces.

Ligands are found based on pyrene compounds, such as pyrenobutyric acid, pyrenobuttanoic acid, succinymidyl ester, or combinations thereof.

Bifunctional ligands based on pyrene compounds linked to semiconductor joint and target analyte.

In a preferred embodiment, the sensor presents a self-assembled monolayer of pyrenbutyric acid (PyBA) and, at its other end, the target analyte is covalently linked, providing mechanical, chemical, and electronic stability of the detected signal.

The sensor object of the present invention reaches an estimated detection limit (LOD) of $0.997/n$ mM/L (where n is the number of unit sensors used in an array-type configuration), with high sensitivity in transconductance in the order of 0.75-1.5 S for 1-3 UDP-glucose molecules, with low input (VG-0.9V) and output (VDS×0.1V) voltages.

In this sense, an array of nanosensors of 1000×1000 units would result in a LOD s 0.997 nM/L.

The sensor object of the present invention employs different types of bifunctional ligands to selectively link and detect other biomarkers, which, allows to make portable arrays of sensors and other applications with emerging needs with high performance detection, field diagnostics, real-time analysis, low cost, high mobility and minimum calibration requirements.

In a more particular realization of the invention, for applications in biosensors, the device presents a two-dimensional hexagonal structure and a carbon atom in thickness, in the form of honeycomb, on an atomic scale.

GNR's configure the semiconductor joint of the sensor and have controlled geometric conditions where the thickness of that semiconductor joint defines the electronic transport properties of the material.

The device also has a metal gate separated from the channel by a dielectric material. In a preferred embodiment of the invention, the dielectric material is selected between boron nitride and silicon dioxide; this dielectric material is located between the base gate and the semiconductor joint.

The invention features a high-density design with thermionic conduction and geometry-controlled electronic belt gap (semiconductor channel length and width, respectively).

In a preferred embodiment of the invention, the width of the GNR is between 9 to 10 atoms thick and the length equal to or greater than 6 nanometers.

The device object of the invention has the possibility to use different bifunctional binders that can be self-assembled to the graphene channel and therefore link different types of target molecules for detection.

The base architecture of the device can be part of a sensor arrangement, in multiple logical combinations, for real-time fusion and processing of sensing signals.

The sensor design allows the creation of combinatorial logics (AND, OR, XOR, and complex functions) of biological signals, given by the measurement of different analytes/biomarkers.

The general node architecture to form biomarker sensing arrangements incorporated by the sensor object of the invention, allows selective detection and very low concentrations of analytes (pM-nM) with an estimated detection limit of 0.997/n mM/L (where n corresponds to the number of units of the sensing node in an array configuration).

The sensor design enables the synthesis of complex, high-density combinatory circuits for real-time processing and analysis of the content of analyte fractions in solution.

The device object of the invention is of nodal type with the ability to distinguish in resolution up to one (1) target molecule (analite), with conductance between 0.75-1.5 oS for 1-3 molecules from UDP-glucose to VG-0.9V and output voltage of VDS×0.1V.

The device is completely bio-compatible, because it is based exclusively on carbon-based materials, which allows its application in ex vivo sensing techniques, as well as its potential application for in-vivo measurements.

The device design allows the manufacture of high-resolution biomarker sensors by bottom-up synthesis or top-down manufacturing.

The sensor disclosed in the present invention, by not requiring prior chemical marking of the sensing objective and, by detecting low concentrations of biologically significant molecular substances, without inducing immune responses, simplifies conducting experiments, minimizes detection errors, improves observations in real time and reduces the overall costs of examining the health of living organisms.

The device also has a metal gate separated from the channel by a dielectric material with relative permittivity of $\varepsilon T=4\varepsilon 0$, where $\varepsilon 0=8.8541878176\times 10-12$ F/m is vacuum's permittivity.

The examples described below are presented with the aim of describing the preferred aspects of the invention, but do not constitute a limitation within the scope of the invention.

Example 1

Through in-silico screening, the optimal ac-GNR g-FET geometric characteristics (e.g., channel or joint width and length) are established for optimal detection of target analytes, and the thermodynamic stability of the system is confirmed at room temperature.

As seen in FIG. 1(a), the channel and electrodes of the device consist of GNRs with Armchair edge. Geometric conditions are controlled as follows:

The width is controlled to obtain semiconductor (finite energy gap) or quasi-metallic (energy gap near zero) properties, respectively.

This behavior is obtained in a device with WC channel width of 10 carbon atoms (~1.1 nm) and WL electrode width of 17 carbon atoms (2 nm).

Figure 1B:
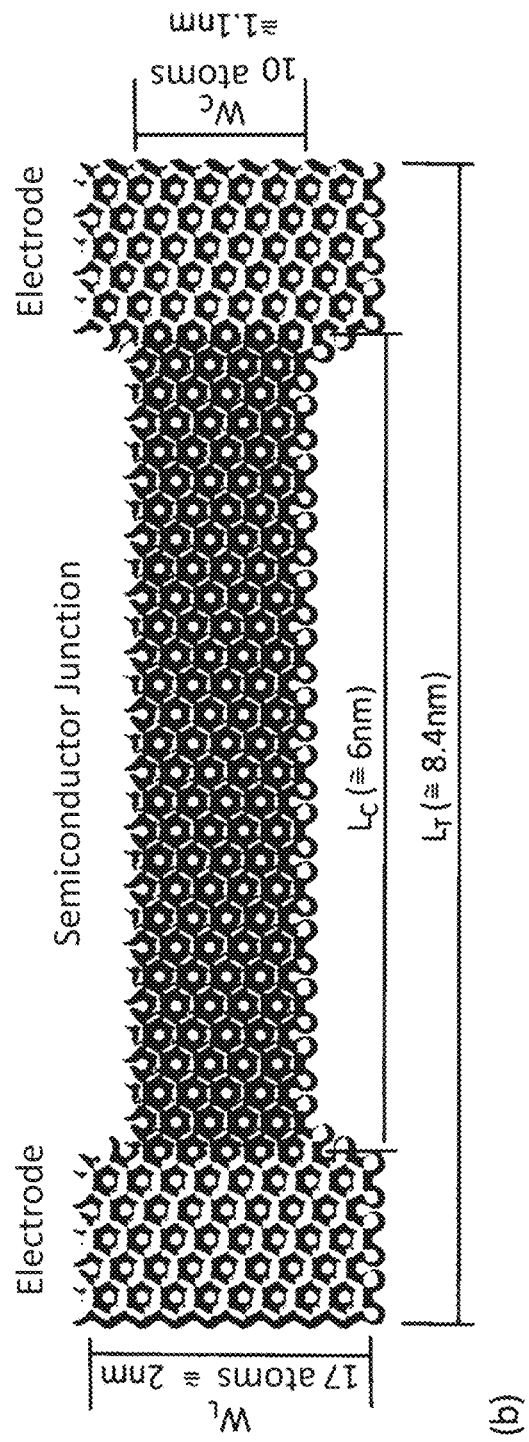
FIG. 1b. Top view of the device with the sample of its geometry with its length and width control to achieve the desired electronic transport properties. Graphene nano-tape are armchair type.
Figure 2:
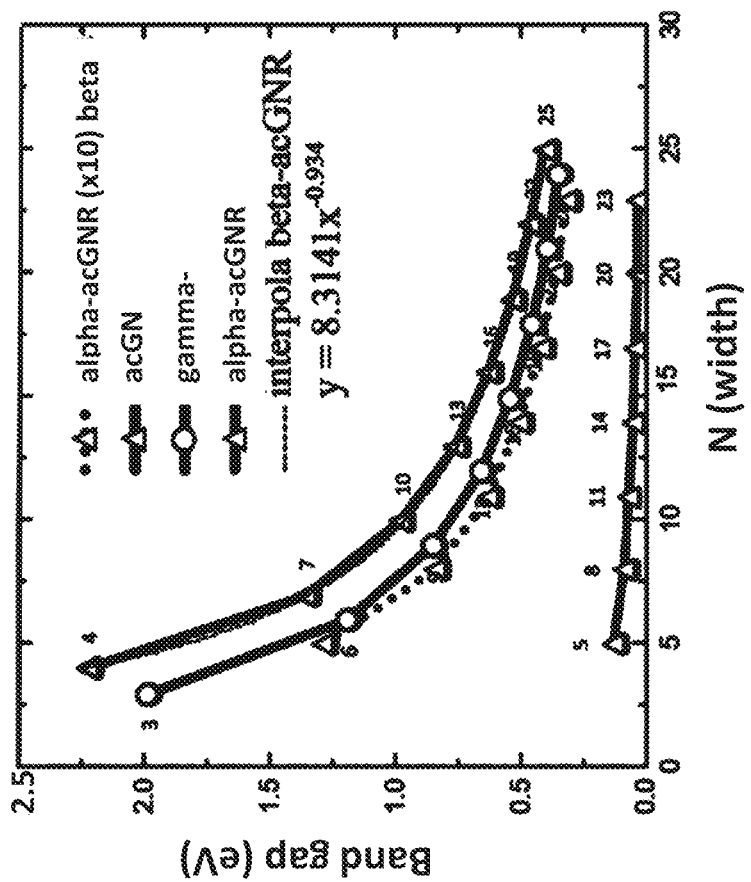
FIG. 2. It shows the belt gaps in the electronic transport of armchair graphene nano-tapes with different widths. The width geometric condition control defines the metallic or semiconductor state of the nano-tape.

The central region of the device has a solvent well that allows the interaction of semiconductor GNR with external molecules. Thus, the channel of the device, with LC width of 6 nm, is functionalized with PyBA molecules through 7-7 stacking between the pyrene and the surface of the GNR, as shown in FIG. 1(b), at a distance of approximately 3.2 Å and standard deviation of 0.08 Å.

In turn, the other end of the PyBA is used to covalently bind to a UDP-glucose molecule, whose link has an average distance of 1.5 Å. In this way, the surface of graphene in the channel, exposed to the solvent well, allows thermodynamically stable functionalization with a monolayer of up to 4 PyBA molecules, where a maximum of 3 UDP-glucose molecules can be linked and detected later.

Example 2

Figure 3:
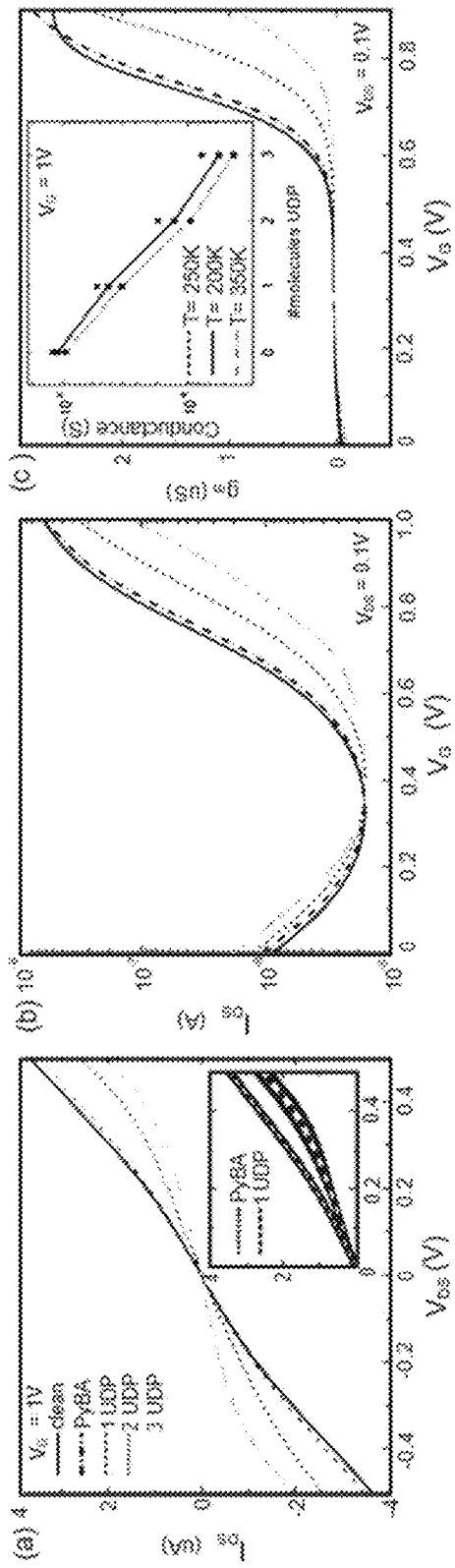
FIG. 3. A) Displays the voltage current characteristics of the device without and with pyrenobutyric acids and with UDP glucose molecules bound to them. The figure compares the difference in electronic response to the presence of udp glucose molecules. B) Shows the effect of positive doping on transconductance based on increased concentration of UDP glucose molecules. C) Displays the transconductance curve vs bias voltage at the input.

FIG. 3 shows the performance of the device with 4 self-assembled PyBA molecules and 0-3 UDP-glucose molecules bound to the opposite end of 3 of the available PyBA molecules, so that the panel (a) shows the current-voltage characteristics with input voltage VG-1V, the panel (b) shows the current based on VG and the panel (c) shows the transconductance based on VG, as well as the variation in the conductance of the device with VG-1V and 3 different temperatures, T-250, 300, 350K.

This shows that functionalization with PyBA molecules does not alter the electronic transport properties of the clean device, which is critical to achieving a detection signal independent of the self-assembled binder layer.

For its part, a greater number of UDP-glucose molecules changes the device's transconductance response and moves it to the right, which is equivalent to having a p-type doping, so that very low voltages VG-0.85V and VDS-0.1V are sufficient to distinguish different concentrations of the analyte, thanks to differences in the range of 0.75-1.5 oS for 1-3 molecules of UDP-glucose.

According to Green's out-of-balance (NEGF) function formalism, the application of a potential differential between the drainage and source electrodes in the field effect device of the present invention, generates a different electrochemical potential between them, so that the function of electronic transmission through the channel is given by the probability of transmitting an electron between the electrodes.

In this way, the current through the device depends on the difference in potential between the electrodes and the electronic transmission function inherent in graphene, which in the invention device is modulated close to the ignition threshold through the gate electrode and in the linear ignition region by the number of analytes linked on the binding molecules in the semiconductor joint.

This results in an electronic signal proportional to the concentration and an adequate on/off ratio.

The characteristics of Current Vs. Voltage of the device of the invention demonstrate that the self-assembled layer of binding molecules (butyric pyrene acids, PyBA) does not affect the properties of electronic transport through the channel or semiconductor joint.

This allows obtaining a proportional and "pure" electronic signal associated with the number of analytes covalently linked to the PyBAs on the semiconductor channel.

Similarly, the device's transfer conductance (or transconductance) characteristics identify the difference in analyte concentration, as it is equivalent to a type-p (positive) doping, identified by the right shift of the transconductance curves due to the increase in concentration, as shown in FIG. 3b). A difference is observed between the conductance value based on the concentration of UDP glucose molecules at a bias voltage of 0.9 volts.

This allows to differentiate molecular concentrations at relatively low operating voltages, just 0.85 V in gate voltage and 0.1 V in the voltage between source and drain.

These features are useful for biological applications, IoT (Internet of Things) mobile devices, among many others with low power consumption requirements.

Example 3

Starch was detected by modifying functional ligands. The ligands selected for this purpose were succinnimdylic ester and pyrenobutanoic acid.

Under these conditions it is feasible to infer that the sensor subject of the present invention is useful in simple metabolite detection procedures in different types of living organisms.

Although the present invention has been described with the preferred realizations shown, it is understood that modifications and variations that preserve the spirit and scope of this invention are understood within the scope of the attached claims.

The invention claimed is:

1. A field-effect sensor for the detection and measurement of simple metabolites and sensing of molecules in organisms, the sensor comprising:
a field-effect transistor consisting of a two-dimensional central channel between carbon-based electrodes, said two-dimensional central channel being composed of carbon semiconducting nanoribbons and is exposed on one side to a solvent containing target analytes and on an opposite side to a dielectric material which in turn is connected to a base gate made of a carbon-based metallic material, wherein the dielectric material separates the base gate from a side of the two-dimensional central channel opposite to the side exposed to the solvent; said target analytes and a surface of the side of the two-dimensional central channel exposed to the solvent are bound by bifunctional ligands based on pyrene compounds; and a length and width of the two-dimensional central channel are controlled to determine a thermionic conduction and an electronic band gap of the sensor, respectively.

2. The field-effect sensor according to claim 1, wherein the two-dimensional central channel is a graphene nanoribbon with an armchair-type edge.

3. The field-effect sensor according to claim 1, wherein the carbon-based electrodes are graphene nanoribbons with an armchair-type edge.

4. The field-effect sensor according to claim 1, wherein the two-dimensional central channel and the carbon-based electrodes are graphene nanoribbons with an armchair-type edge.

5. The field-effect sensor according to claim 1, wherein the carbon-based electrodes are graphene nanoribbons with a zigzag edge, or of metallic material.

6. The field-effect sensor according to claim 1, wherein said dielectric material is selected from boron nitride, silicon dioxide, or transition metal oxides.

7. The field-effect sensor according to claim 1, wherein said two-dimensional central channel has a width of 9 or 10 atoms.

8. The field-effect sensor according to claim 1, wherein said two-dimensional central channel has a length equal to or greater than 6 nanometers.

9. The field-effect sensor according to claim 1, wherein said bifunctional ligands are selected from a group consisting of pyrenobutyric acid, pyrenobutanoic acid, succinimidyl ester, or combinations thereof.

10. The field-effect sensor according to claim 1, characterized by a self-assembled monolayer of said bifunctional ligands based on pyrene compounds with pyrenobutyric acids (PyBA's) that chemically modifies the surface of the side of the two-dimensional central channel exposed to the solvent without altering its electron transport properties.

* * * * *